US00PP32516P2

(12) United States Plant Patent
Lee

(10) Patent No.: US PP32,516 P2
(45) Date of Patent: Nov. 24, 2020

(54) ***GARDENIA* PLANT NAMED 'LEEFIVE'**

(50) Latin Name: *Gardenia hybrida*
Varietal Denomination: LEEFIVE

(71) Applicant: Robert Edward Lee, Independence, LA (US)

(72) Inventor: Robert Edward Lee, Independence, LA (US)

(73) Assignee: PDSI, Loxley, AL (US)

( * ) Notice: Subject to any disclaimer, the term of this patent is extended or adjusted under 35 U.S.C. 154(b) by 0 days.

(21) Appl. No.: 16/602,969

(22) Filed: Jan. 7, 2020

(51) Int. Cl.
*A01H 5/02* (2018.01)
*A01H 6/76* (2018.01)

(52) U.S. Cl.
USPC ..... Plt./255

(58) Field of Classification Search
USPC ..... Plt./226, 255
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct cultivar of *Gardenia* plant named 'LEEFIVE' is disclosed, characterized by a distinctive columnar plant habit. Foliage is very glossy, broadly ovate and uniquely crinkled. Flowering will occur on a rebloom-ing cycle Summer and Fall. Plants are compact, dense and suitable for Southern climates. The new cultivar is a *Gardenia*, suitable for ornamental garden purposes.

2 Drawing Sheets

Latin name of the genus and species: *Gardenia hybrida*.
Variety denomination: 'LEEFIVE'.

BACKGROUND OF THE INVENTION

The new cultivar is a product of a planned breeding program by the inventor. This new variety, hereinafter referred to as 'LEEFIVE', was found as the result of an open pollination conducted during 2007 which included a group of unnamed, unpatented *Gardenia hybrida* plants as parents. The inventor discovered the unique seedling in Independence, La., at a research nursery during Spring of 2010.

After identifying the new variety as a potentially interesting selection, the inventor first organized propagation of 'LEEFIVE' by semi-hardwood cuttings during Fall of 2010 at the same nursery in Independence, La. The inventor continued confidential, controlled testing and propagation, assessing stability of the unique characteristics of this variety. Multiple generations have been reproduced and have shown that the unique features of this cultivar are stable and reproduced true to type.

SUMMARY OF THE INVENTION

The cultivar 'LEEFIVE' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'LEEFIVE' These characteristics in combination distinguish 'LEEFIVE' as a new and distinct *Gardenia* cultivar:

1. Unique columnar growth habit.
2. Tolerance for heat stress.
3. Adaptability to production and use in Southern climates.

4. Very shiny leaves.
5. Ovate, moderately crinkled foliage.
6. Repeat blooming in Summer and Fall.
7. Good specimen plant.
8. Good container plant.

COMPARISON TO PARENT VARIETY

The parent varieties are unidentified.

COMMERCIAL COMPARISON

'LEEFIVE' can be compared to the commercial variety *Gardenia hybrida* 'LEETHREE', U.S. Plant Pat. No. 27,599. Plants of the new cultivar 'LEEFIVE' are similar to plants of 'LEETHREE' in most horticultural characteristics, however, plants of the new cultivar 'LEEFIVE' differ in the following:

1. While both plants have compact growth, the new variety grows taller and narrower, in a columnar habit, compared to the rounded habit of 'LEETHREE'.
2. 'LEEFIVE' produces large diameter flowers than 'LEETHREE'.

'LEEFIVE' can be compared to the commercial variety *Gardenia hybrida* 'LEETWO', U.S. Plant Pat. No. 27,601. Plants of the new cultivar 'LEEFIVE' are similar to plants of 'LEETWO' in most horticultural characteristics, however, plants of the new cultivar 'LEEFIVE' differ in the following:

1. While both plants have compact growth, the new variety grows taller and narrower, in a columnar habit, compared to the globular habit of 'LEETWO'.
2. 'LEEFIVE' produces large diameter flowers than 'LEETWO'.

BRIEF DESCRIPTION OF THE PHOTOGRAPHS

Figure 1:
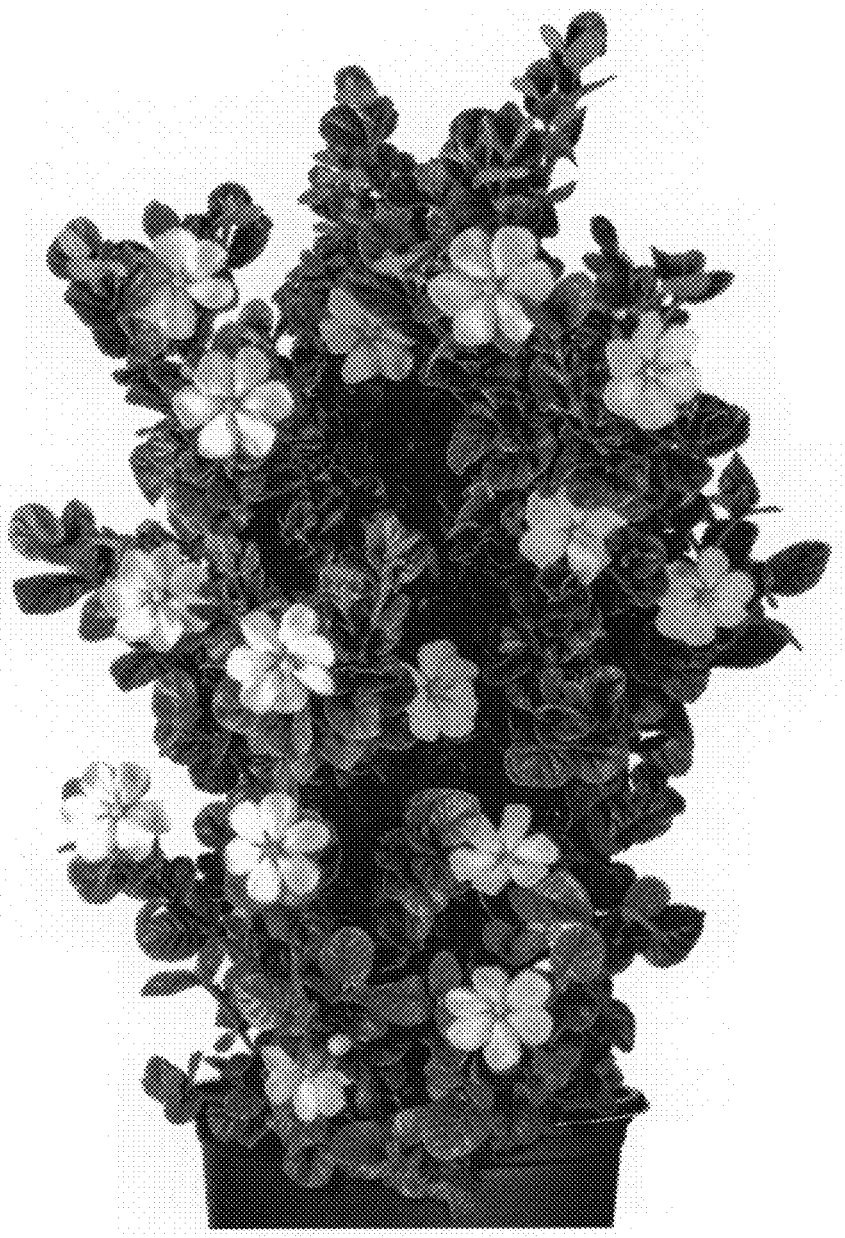

The accompanying photograph in FIG. 1 illustrates in full color a plant of 'LEEFIVE' grown outdoors in Alabama.

Figure 2:
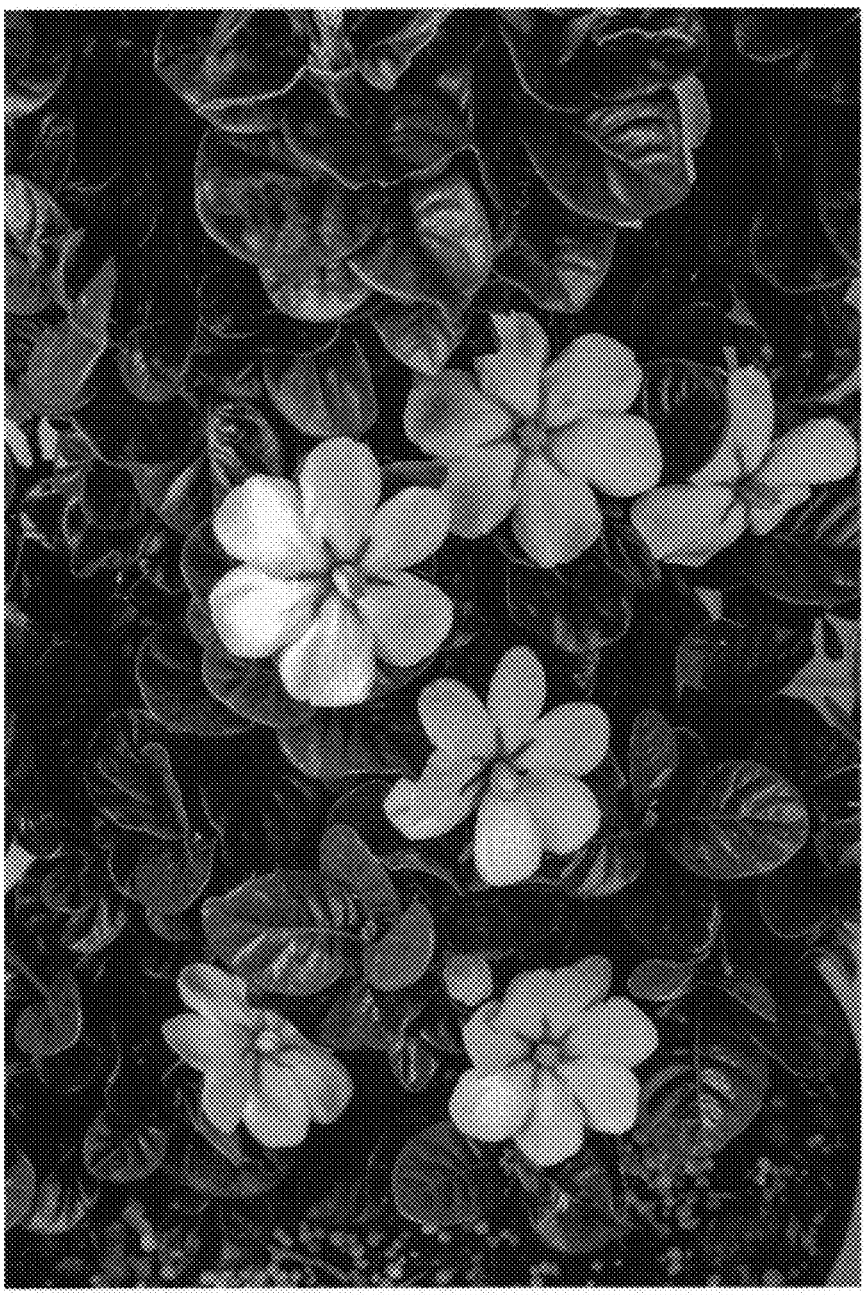

FIG. 2 shows a close up of typical flowers of the new variety. The plant is approximately 2 years old, and is shown in a three-gallon container.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'LEEFIVE' plants grown outdoors in Loxley, Ala. Plants are approximately 2 years old, in a 3 gallon nursery container. Measurements and numerical values represent averages of typical plant types.

Botanical classification: *Gardenia hybrida* 'LEEFIVE'.

PROPAGATION

Typically by semi-hardwood cuttings in Spring and Summer.

Root description: Woody to semi-wood. Colored near RHS Brown 200D.

Time to initiate roots: About 4 to 6 weeks in the Summer.

Time to produce a rooted young plant: Approximately 12 weeks in the Summer.

PLANT

Growth habit: Columnar shrub.

Height: Approximately 52 cm to top of foliar and flowering plane.

Plant spread: Approximately 28 cm.

Branching characteristics: Well branched, approximately 4 to 6 lateral branches emerge from a pinch. Some smaller lateral branches occurring with pinch. Branches occur at upright angles, approximately 15° to 35° from center.

Primary branches:

Length of primary branches: Average 6-8 cm, then pinched and new branches emerge.

Dimeter of primary branches: Approximately 0.9 cm.

Primary branch strength: Very strong, flexible, difficult to break.

Primary branch color:

*Mature branches*.—Near RHS Grey-Brown 199B with striation near Greyed-Purple 183C.

*Young branches*.—Near RHS Yellow-Green 145A.

Primary branch texture:

*Mature branches*.—Rough.

*Young growth*.—Glabrous.

Lateral branches:

*Color*.—Near RHS Grey-Brown 199A.

*Length*.—Average range 10 to 21 cm.

*Diameter*.—Approximately 0.8 cm.

*Aspect*.—Straight, attached at acute angles.

*Texture*.—Slightly canescent.

*Strength*.—Strong, flexible.

*Internode*.—Average range 0.8 cm to 2.1 cm.

Age of plant described: Approximately 2 years.

FOLIAGE

Leaf:

*Type*.—Simple.

*Arrangement*.—Opposite. At end of branches tightly spaced, to appear whorled.

*Average length*.—3.5 to 4.8 cm.

*Average width*.—3.3 to 4.5 cm.

*Shape of blade*.—Broad ovate.

*Apex*.—Blunt rounded or broad acute.

*Base*.—Cuneate.

*Attachment*.—Sessile.

*Margin*.—Entire.

*Aspect*.—Strong undulation in older leaves. Weak undulation in younger leaves.

*Internode*.—Average 0.5 to 1.0 cm.

*Texture of top surface*.—Glabrous.

*Texture of bottom surface*.—Glabrous.

*Appearance of top surface*.—Very glossy.

*Appearance of bottom surface*.—Matte.

*Color*.—Young foliage upper side: Near RHS Yellow-Green 146B. Young foliage under side: Near RHS Green 138B. Mature foliage upper side: Near RHS Green 139A. Mature foliage under side: Near RHS Green 138B.

*Venation*.—Type: Pinnate. Venation color upper side: Near RHS Green 143C. Venation color under side: Near RHS Yellow-Green 144B.

FLOWER

Bloom period: Plants flower in the Spring, then begin intermittent flowering cycles in late Spring/Summer through Fall.

Inflorescence:

*Arrangement*.—Single rotate flowers arise from upper leaf axils.

Peduncle:

*Length*.—Average range 0.9 to 1.4 cm.

*Diameter*.—0.4 cm.

*Color*.—Near RHS Green 143B.

*Texture*.—Glabrous.

*Aspect*.—Straight. Angle of attachment, approximately 0 to 15° angle from stem.

*Strength*.—Moderately strong and flexible.

Flowers:

*Arrangement*.—Single rotate flowers arise from upper leaf axils.

*Length*.—Average 3.5 cm.

*Diameter*.—Average 5.5 cm.

*Facing direction*.—Outwardly facing.

*Persistent or self-cleaning*.—Flowers persist until completely dried up, then fall off.

*Fragrance*.—Strong, sweet fragrance.

Tube:

*Tube length*.—Approximately 2.9 cm.

*Tube width a widest point*.—Approximately 0.5 cm.

*Tube width and narrowest point*.—Approximately 0.3 cm.

Petals:

*Unfused petal segments*.—

*Length*.—Approximately 2.8 cm.

*Width*.—Approximately 1.6 cm.

*Apex*.—Rounded.

*Base*.—Fused at base into tube.

*Shape of petal*.—Unfused portion, spatulate.

*Petal margin*.—Entire.

*Petal arrangement*.—Rotate, slightly overlapping, fused approximately ⅓ from base.

*Petal number*.—6.

*Petal texture*.—Smooth, upper and lower surfaces.

*Color*.—Upper surface at first opening: Near RHS White 155C. Under surface at first opening: Near RHS White 155C. Inner surface at maturity: Near RHS White 155C. Outer surface at maturity: Near RHS White 155C. Upper surface at fading: Near RHS White 155C. Under surface at fading: Near RHS White 155C.

Bud:

*Shape*.—Elliptic.

*Length*.—2.8 cm.

*Diameter*.—1.7 cm.

*Color*.—Near RHS White 155C and Yellow-Green 150D.

Calyx/sepals:

*Quantity per flower*.—5 sepals.

*Arrangement*.—Rotate.

*Shape*.—Narrow deltate, base fused.

*Length*.—Average 1.1 cm.

*Width*.—0.3 cm.

*Apex*.—Acute.

*Base*.—Fused.

*Margin*.—Entire.

*Texture*.—Very slightly pubescent all surfaces.

*Color*.—Inner Surface: Near RHS Green 143C. Outer Surface: Near RHS Green 137D.

REPRODUCTIVE ORGANS

Stamens:

*Number*.—6, except anthers, androecium fused to floral tube.

*Length*.—0.9 cm, anthers only.

*Width*.—0.1 cm.

*Anthers*.—Anthers reflexed back, and attached to petals. Length: Approximately 0.9 cm. Width: Approximately 0.1 cm. Color: Near RHS Greyed-Orange 155B. Pollen: Scant, colored near RHS Greyed-Orange 165D. Shape: Linear to crescent.

Pistil:

*Number*.—1.

*Length*.—3.7 cm.

*Style*.—Length: 3.1 cm. Color: Near RHS Yellow-Green 150D.

*Stigma*.—4 lobed globular, colored near RHS Greyed-Yellow 160D.

*Ovary*.—Approximately 0.4 cm in diameter, 0.4 long. Colored near RHS Green 143B.

OTHER CHARACTERISTICS

Disease and pest resistance: Neither resistance nor susceptibility observed to normal diseases and pests of *Gardenia hybrida*. Typical diseases of *Gardenia* include *Erysiphe polygoni*, and *Phomopsis gardenia*. Pests include the nematode *Meloidogyne* spp., white fly *Dialeurodes citri* and various scales, including *Ceroplastes japonicas, Icerya purchase, Fiorinia theae, Hemiberlesia rapax* and *Aspidiotus nerii*.

Temperature tolerance: USDA Zone 7 to 10.

Fruit/seed production: Not observed to date.

What is claimed is:

1. A new and distinct cultivar of *Gardenia* plant named 'LEEFIVE' as herein illustrated and described.

* * * * *